(12) United States Patent
Hall et al.

(10) Patent No.: US 9,867,513 B1
(45) Date of Patent: Jan. 16, 2018

(54) MEDICAL TOILET WITH USER AUTHENTICATION

(71) Applicants: David R. Hall, Provo, UT (US); Dan Allen, Springville, UT (US); Andrew Davis, Provo, UT (US)

(72) Inventors: David R. Hall, Provo, UT (US); Dan Allen, Springville, UT (US); Andrew Davis, Provo, UT (US)

( * ) Notice: Subject to any disclaimer, the term of this patent is extended or adjusted under 35 U.S.C. 154(b) by 0 days.

(21) Appl. No.: 15/257,014

(22) Filed: Sep. 6, 2016

(51) Int. Cl.
*A47K 13/24* (2006.01)
*A47K 17/02* (2006.01)
*G06K 9/00* (2006.01)
*G06F 3/16* (2006.01)
*G06F 19/00* (2011.01)
*A61B 10/00* (2006.01)
*A61B 5/00* (2006.01)
*A61B 5/20* (2006.01)

(52) U.S. Cl.
CPC ............. *A47K 13/24* (2013.01); *A47K 17/02* (2013.01); *G06F 3/16* (2013.01); *G06F 19/3406* (2013.01); *G06K 9/00033* (2013.01); *G06K 9/00926* (2013.01); *A61B 5/207* (2013.01); *A61B 5/68* (2013.01); *A61B 10/007* (2013.01); *A61B 10/0038* (2013.01)

(58) Field of Classification Search
CPC ........ G06F 21/32; G06F 3/16; G06F 19/3406; A47K 13/24; A47K 17/02; G06K 9/00033; G06K 9/00926; A61B 5/117; A61B 5/1172; A61B 10/0038; A61B 10/007; A61B 5/207; A61B 5/68
See application file for complete search history.

(56) References Cited

U.S. PATENT DOCUMENTS

| 2009/0216099 | A1* | 8/2009 | Kim | ..................... A61B 5/022 600/345 |
| 2014/0323836 | A1* | 10/2014 | Kusukame | ........... A61B 5/6891 600/344 |

\* cited by examiner

*Primary Examiner* — Kenny Cese (57) ABSTRACT

A medical toilet with fingerprint reading handles is disclosed. The handles extend from a side surface of a seat on the medical toilet allowing a toilet seat user to use the fingerprint reader while sitting on the medical toilet. The handles enable authentication of a user and loading of specific medical toilet functionality associated with the authenticated user. The fingerprint readers are also used to determine cardiac functions of the user in addition to authentication of the user. The handles may be retractable and may include UV sanitation.

9 Claims, 10 Drawing Sheets

MEDICAL TOILET WITH USER AUTHENTICATION

TECHNICAL FIELD

The present invention relates generally to using handles in toilet seats for user fingerprinting, identification, and medical purposes.

BACKGROUND

Assessment of a person's functional ability, physical health, cognition, and mental health is usually initiated when a physician identifies a potential problem. Specific elements of physical health that may be evaluated include nutrition, vision, hearing, fecal and urinary continence, and balance. Assessment aids in diagnosis of medical conditions, development of treatment and follow-up plans, coordination of management of care, and evaluation of any long-term care needs.

One problem with assessment is that it can take time, requiring a person's time and the time of his or her physician. Another problem with assessments is that, because of demands of a busy clinical practice, many assessments tend to be less comprehensive and more problem-directed. Assessment can also be inconvenient for a person being assessed and/or for his or her physician as one or both may need to travel for the assessment. Additionally, assessments may be often not as frequent or as regular as would be desired to obtain more comprehensive data, due to the above mentioned problems.

SUMMARY OF THE INVENTION

A medical toilet with fingerprint reading handles is disclosed. The handles extend from a side surface of a seat on the medical toilet allowing a toilet seat user to use the fingerprint reader while sitting on the medical toilet. The handles enable authentication of a user and loading of specific medical toilet functionality associated with the authenticated user. The fingerprint readers are also used to determine cardiac functions of the user in addition to authentication of the user. The handles may be retractable and may include UV sanitation.

A toilet seat is disclosed that overcomes or improves upon the limitations discussed above. In general, a toilet includes a toilet seat with a fingerprint reader in the handle which is used to identify a user of the toilet and used to obtain cardiac function signals of the user. The fingerprint reader can identify a user of the toilet seat, control medical testing functionality of the toilet, monitor cardiac functions of the toilet seat user, and associate authentication data with medical testing data. The toilet seat is positioned on a toilet, and the handles may be attached to the toilet seat such that a user can use them to lower and/or raise himself or herself onto/from the toilet seat. One or more light transmitters and optical imagers within a fingerprint reader may be used to determine blood oxygen saturation levels of the user, heart rate of the user, etc., while also providing an authentication of the toilet user by obtaining fingerprint identification data of the user. The handles serve multiple purposes such as allowing a user to raise and lower himself or herself from a toilet and the handles provide a health monitoring function of determining blood oxygen saturation level, heart rate, diastolic pressure, systolic pressure, fingerprint identification, and enable user authentication for medical testing performed on a user while using the toilet. Handles used to raise and lower individuals do not currently preform the above medical monitoring, identification, and user authentication functions. A user account may also be created which stores user authentication information, medical information related to toilet medical testing, user settings, and medical database health information.

In one embodiment, a toilet seat is disclosed which includes a fingerprint reader in a handle. The fingerprint reader may be a non-contact type optical reader such as a camera or capacitive coupled display (CCD) imager. The handles may include one or more light transmitters and optical imagers. The fingerprint reader may be located within a recessed area of a toilet seat handle allowing a user to access the reader without touching a surface of the handle.

Commonly owned medial toilet patent applications titled "Excreta-Sampling and Chilling Toilet" application Ser. No. 15/248,788; "Toilet Volatile Organic Compound Analysis System for Urine" application Ser. No. 15/250,039; "Health Condition Determination System" application Ser. No. 15/242,929; and "User Identifying Toilet Apparatus" application Ser. No. 15/150,797 are hereby incorporated by reference for all that they teach.

BRIEF DESCRIPTION OF THE DRAWINGS

A more particular description of the invention briefly described above is made below by reference to specific embodiments. Several embodiments may be depicted in drawings included with this application, in which.

DETAILED DESCRIPTION

A detailed description of the claimed invention is provided below by example, with reference to embodiments in the appended figures. Those of skill in the art will recognize that the components of the invention as described by example in the figures below could be arranged and designed in a wide variety of different configurations. Thus, the detailed description of the embodiments in the figures is merely representative of embodiments of the invention, and is not intended to limit the scope of the invention as claimed.

In some instances, features represented by numerical values, such as dimensions, mass, quantities, and other properties that can be represented numerically, may be stated as approximations. Unless otherwise stated, an approximate value means "correct to within 50% of the stated value." Thus, a length of approximately 1 inch should be read "1 inch+/−0.5 inch."

Aspects of the present invention may be described herein with reference to flowchart illustrations and/or block diagrams of methods, toilet seat (systems), and computer program products according to embodiments of the invention. Those of skill in the art will understand that each block of the flowchart illustrations and/or block diagrams, and combinations of blocks in the flowchart illustrations and/or block diagrams, may be implemented by computer readable program instructions. Additionally, those of skill in the art will recognize that the system blocks and method flowcharts, though depicted in a certain order, may be organized in a different order and/or configuration without departing from the substance of the claimed invention.

Figure 1:
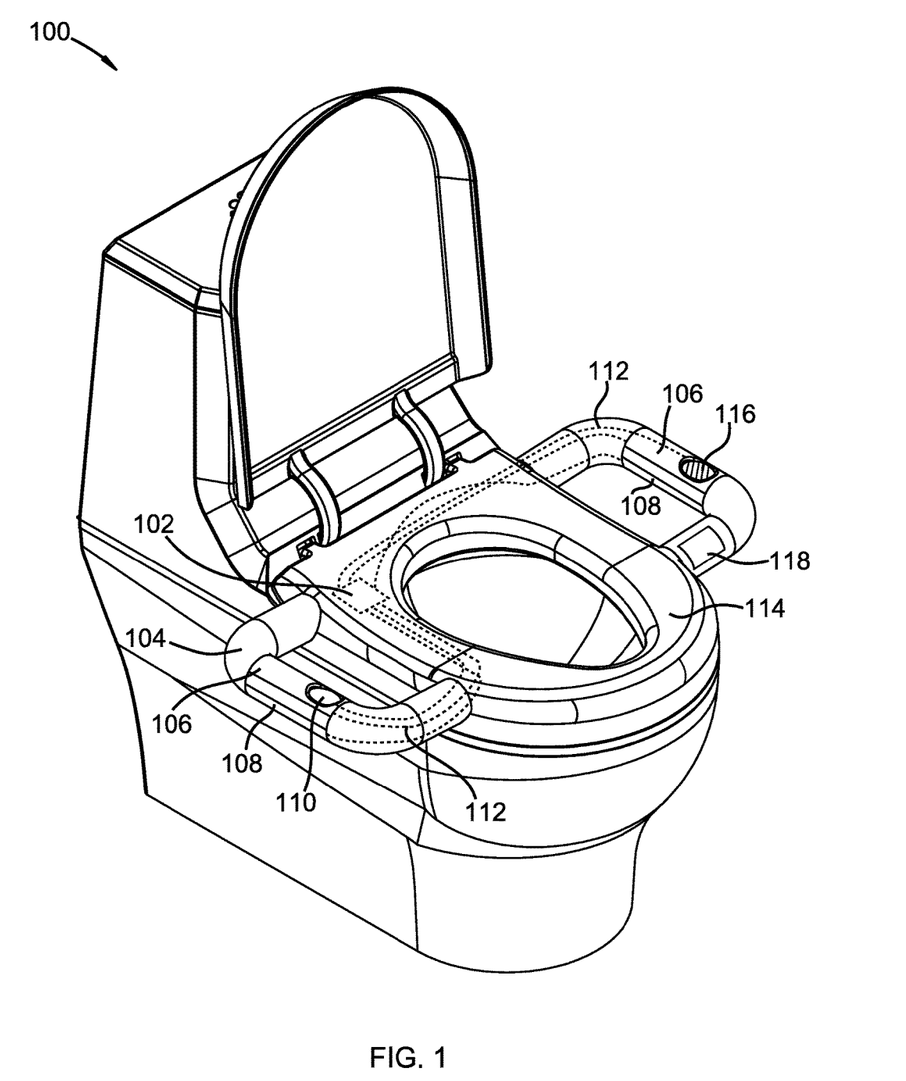
FIG. 1 depicts a toilet with a toilet seat having a handle and display.

FIG. 1 depicts a medical toilet 100 with toilet seat handles 104, fingerprint readers 116/110, display 118, controller/processor 102, and wires 112. Toilet seat 114 includes handles 104 which extend from sides of the toilet seat. Fingerprint readers 116/110 may be used as photoplethysmography (PPG) sensors to determine cardiac functions such as blood oxygen saturation level, heart rate, diastolic pressure, and systolic pressure. PPG detectors may be capacitive coupled display (CCD) imagers such as a camera imager used to detect change in tissue color. Blood absorbs light, so if more blood is in tissue, then less light can transmit through it resulting in reflected or transmitted light color changes based on blood profusion as blood is pulsed or pumped through capillaries.

In some embodiments, a transmission PPG sensing operation is utilized. In these embodiments, fingerprint reader 110 may emit light at wavelengths between visible and infrared spectrums. Fingerprint reader 110 may be positioned on one side of a finger and light receivers or imagers may be positioned on an opposite side of the finger. When arterial blood flows into the finger, the finger fills with blood. When the blood is oxygenated, absorption specific to oxy-hemoglobin is relatively high. When blood is deoxygenated, absorption specific to deoxy-hemoglobin is high. A relation between changing amplitudes of light intensity with each heart beat is used to estimate blood oxygen saturation level. Heart rate is also estimated by observing the periodicity in the light transmission or reflection intensity at a single color, or averaged over many colors. In some further embodiments, light transmitters within fingerprint reader 110 may be light emitting diodes (LEDs), white light generators, halogen lights, and/or lasers. The light receivers or imagers may be photodiodes, capacitive coupled displays (CCDs), or CMOS imagers. In other embodiments, a first handle houses one or more optical sensors which interface with a hand of a user of the toilet seat while the user is sitting on a toilet. A second handle may be used to house one or more optical sensors. Fingerprint sensors may also include light transmitters and light receivers for determining cardiac functions such as blood oxygen saturation level, heart rate, diastolic pressure, systolic pressure, in addition to surface texture and features of a fingerprint. Light sources used with the fingerprint sensors may include white light sources, LED light sources, and laser light sources. The first and/or the second handles may retract and extend into and from a side surface of the toilet seat. UV sanitation may be employed to sanitize the handles while the handles are in a retracted state.

In some embodiments, a reflection PPG sensing operation is utilized. In these embodiments, fingerprint readers employing light transmitters may be positioned on one side of a finger and light receivers may be positioned on the same side of the finger. (Shown in FIG. 9B). In this arrangement, the light transmitters emit light which transmits through one or more top surfaces of tissue and reflects off a lower layer to return to light receivers. Perfusion in capillaries near a surface of skin changes with each heartbeat with phase inverted to transmission PPG sensing. To avoid deep penetration typical of IR wavelengths, which would make a light transmission signal sensitive to arterial behavior and thus reduce the signal resolution due to partial cancellation of an opposing capillary and arterial signals, shorter wavelengths may be desirable. For example, in some further embodiments, light emitted from fingerprint reader 110 is blue, green, yellow and/or red.

Blood pressure changes cyclically with each heartbeat. A high pressure point is systolic pressure and a low pressure point is diastolic pressure. When arteries are inelastic, a heart has to push harder to move a same volume of blood, so a resulting pressure in blood vessels increases. A heart beat causes a pressure wave that propagates from heart to body. A pressure is strongest near the heart and is more easily observed in arteries lying close to a surface.

Blood pressure is related to pulse wave velocity (PWV). PWV is related to pulse transit time (PTT) such that PWV=distance/PTT. A PPG signal measured, for example, on a finger is delayed relative to a time difference between PPG signals at locations at different distances from a heart. A pulse wave is identified at a first time by a fingerprint reader 110 at one position on handle 104. The same pulse wave is identified at a second time by a second fingerprint reader 110 at a different position on handle 104. Due to a change in time between time the first and the second pulse times, PTT is determined. Additionally, due to a difference of distance between the locations of the body where the sets of fingerprint readers are located, PWV can be calculated. Subsequently, blood pressure can be estimated from PTT and PWV.

In some embodiments, toilet seat 114 includes two handles 104, each having multiple fingerprint readers 110. Blood pressure is then estimated using PTT of a pulse between the two handles.

In some embodiments, toilet seat 114 includes two handles 104. When a user sits on toilet seat 114, he or she uses handles 104 to seat himself or herself and/or to rise from toilet seat 114. Handles 104 may be also used to stabilize the user while on toilet seat 114.

In some embodiments, fingerprint readers 110 may be positioned under a transparent surface. In other embodiments, fingerprint readers 110 may be positioned geometrically normal to a face of handle 104. In yet other embodiments, handle 104 includes a cavity covered by transparent material. Fingerprint readers 110 may be positioned inside the cavity facing the transparent material.

In some embodiments, handle 104 includes a lenticular lens 116 behind which fingerprint readers 110 may be placed.

In some embodiments, toilet seat 114 includes two handles 104. Each of handles 104 includes fingerprint readers. In a further embodiment, toilet seat 114 includes more than two handles.

In some embodiments, handle 104 includes a first bioimpedance electrode 106 and a second bioimpedance electrode 108. In a further embodiment, toilet seat 114 includes two handles 104, each including a single bioimpedance electrode. In yet further embodiments, handle 104 includes more than two bioimpedance electrodes.

In some embodiments, toilet seat 114 includes controller/processor 102. In these embodiments, toilet seat 114 includes wiring 112 which couples controller 102 to any bioimpedance electrodes, light transmitters, fingerprint readers, and light receivers.

In some embodiments, handle 104 includes ultrasonic transmitters and ultrasonic receivers. The ultrasonic transmitters send sound waves with frequencies from 20 kilohertz (kHz) up to several gigahertz. These transmitters and receivers may be used to estimate bone mineral density. The transmitters emit sound waves into a part of a user's hand, the receivers collect the sound waves leaving the user's hand, and controller 102 calculates how fast the sound waves pass through the user's hand. From this, controller 102 calculates a bone mineral density of the user.

In some embodiments, handle 104 includes one or more pressure sensitive switches. These switches may be positioned such that, when a user places his or her hand on handle 104, fingerprint reader 110 starts taking optical measurements. When the user removes his or her hand from handle 104, fingerprint reader 110 may cease optically transmitting and receiving. In embodiments where handle 104 further includes bioimpedance electrodes, the bioimpedance electrodes also activate and deactivate when the hand of the user is placed on or taken off handle 104.

In some embodiments, toilet seat 114 includes one or more pressure sensitive switches. These switches may be positioned such that, when a user places himself or herself on toilet seat 114, the light transmitters and light receivers actuate to take readings. When the user removes himself or herself from toilet seat 114, a fingerprint reader may turn off. In embodiments where handle 104 further includes bioimpedance electrodes, the bioimpedance electrodes also activate and deactivate when the user places himself or herself on or removes himself or herself from toilet seat 114, respectively.

In some embodiments, toilet seat 100 includes a speaker system which communicates information to a user. When a different positioning of a user's hand or fingers is needed for good readings, the speakers tell the user to reposition his or her hands as needed. Also, the speakers communicate blood oxygen saturation levels, heart rate, diastolic pressure, systolic pressure, etc. to the user.

For example, in some embodiments, a user is interested in whether or not his or her blood oxygen saturation levels have increased or decreased since his or her last time using toilet seat 114. The speaker system receives commands from a controller 102 each time he or she uses toilet seat 114, to inform him or her whether his or her blood oxygen saturation levels have changed or remained the same. Similarly, controller 102 contains instructions for recording previous heart rates, diastolic pressures, systolic pressures, etc. and using said information to compare subsequent data and report on the difference to the user. In some further embodiments, controller 102 includes instructions to compare biometric data obtained from a user for subsequent use, such as for toilet controls and for reporting change in heartrate, bioimpedance measurements, body temperature, blood oxygen saturation levels, diastolic pressure, systolic pressure, etc.

In some embodiments, toilet seat 100 includes one or more microphones which receive information and commands from a user. The user may command that information be stored in memory within toilet seat 114. The user may also command that information be sent to his or her physician. In further embodiments, toilet seat 100 also includes a speaker system. In such embodiments, the speaker system prompts a user for information regarding his or her health. The user's responses may be stored in memory and may be sent to his or her physician. The user may command toilet seat 114 to tell him or her his or her blood oxygen saturation levels, heart rate, diastolic pressure, systolic pressure, etc., and toilet seat 114 will communicate the corresponding information.

In some embodiments, toilet seat 100 includes visual display 118. Visual display 118 may communicate one or more cardiac functions such as blood oxygen saturation levels, heart rate, diastolic pressure, temperature, systolic pressure, etc. to the user. In some further embodiments, toilet seat 100 also includes one or more microphones. A user is prompted by visual display 118 to answer one or more questions, which the user answers audibly or via another peripheral device such as a keyboard or smartphone. In some embodiments, visual display 118 is a touchscreen display.

In some embodiments, toilet seat 114 includes one or more force sensors. These force sensors determine weight distribution of a user. In conjunction with other data, data from the force sensors help determine the balance of the user.

In some embodiments, medical toilet 100 includes one or more handles 104. Handles 104 include one or more force sensors. A user pulls up, pushes down, or pushes out handles 104 to assess his or her strength. This data is used by controller 102 to calculate strength of the user and his or her level of muscular atrophy, if any.

In some embodiments, medical toilet 100 includes fiber optic cable 112 which transports light signals sent by light transmitters 110. For example, in some embodiments, toilet seat 100 includes a single light transmitter 110. Fiber optic cable 112 receives from and transmits signals to fingerprint reader 110.

In some embodiments, toilet seat 100 includes a toilet to which toilet seat 114 is attached. In some embodiments, the toilet includes controller or processor 102 electrically connected to the fingerprint reader programmed to associate the medical toilet, the toilet seat user, a medical functionality of the toilet, and a cardiac function with a user account. In other embodiments, the toilet includes one or more light transmitters, which communicate light signals via fiber optic cable 112 to handles 104.

In some embodiments, handle 104 is retractable into toilet seat 114. After use, handle 104 retracts into toilet seat 114 and one or more of light transmitters 110 emit ultraviolet wavelength rays of light. The ultraviolet rays kill bacteria and partially sanitize handle 104. After a time period specified, which time period is dependent on surface area and geometry of handle 104, handle 104 extends out of toilet seat 114. In some further embodiments wherein toilet seat 100 includes two or more handles 104, all of handles 104 may be retractable into toilet seat 114 and may be treated the same as described above for one handle 104. In some other further embodiments, wherein handle 104 and/or toilet seat 114 include(s) pressure sensitive switches, handle 104 retracts automatically after a user removes himself or herself from toilet seat 114, in response to either opening or closing one or more of the pressure sensitive switches. In some yet further embodiments, a user gives commands to a controller to retract handle 104 by any of a variety of means including a keypad, a visual touch screen display, microphones, a smartphone, etc.

A fingerprint reader 110 may be used to authenticate a user of a medical toilet and associate a medical test with the authenticated user. A toilet may be programmed to perform a specific medical test based on a user identification obtained by fingerprint reader. For example, a doctor may associate a specific test such as a urinalysis, drug test, kidney function test, liver function test, or volatile organic compound test with a specific user identification (fingerprint). When the user's fingerprint is read by a fingerprint reader on a toilet, the toilet may be programmed to perform the medical function (specific test) which a doctor prescribed for the toilet user. The toilet may then authenticate the toilet user and perform the doctor directed testing and report the results to a medical database.

Figure 2:
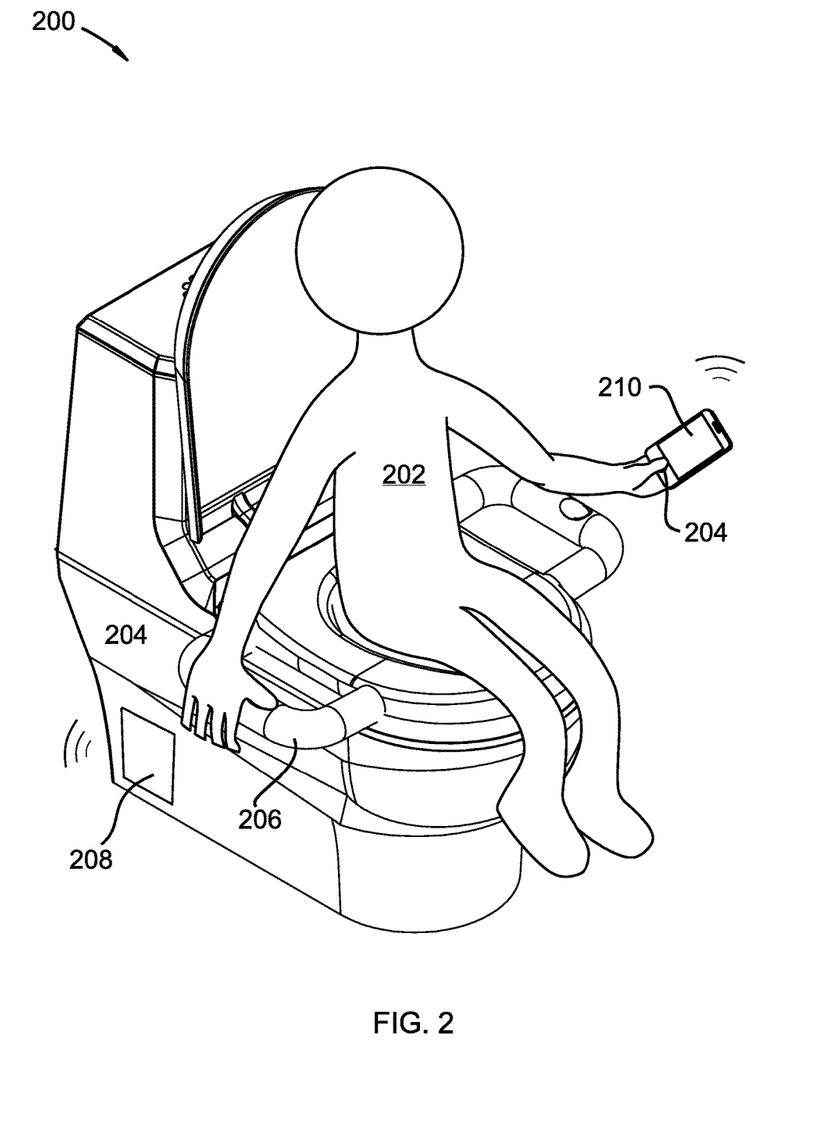
FIG. 2 depicts an embodiment similar to FIG. 1, further including a user.

FIG. 2 depicts an embodiment similar to FIG. 1, further including a user. Toilet seat 200 includes a toilet seat comprising handles 206. As shown, user 202 places hands 204 on handles 206. Hands 204 of user 202 may be positioned such that a fingerprint reader send light signals through hands 204, and light receivers collect any of the light signals which reflect off an interior layer of tissue of hands 204. A user device 210 such as a cell phone or tablet device may be used to associate a user 202 with a medical toilet 200. A fingerprint reader 204 on user device 210 may be used to authenticate a toilet user and load medical testing into toilet controller 208. Toilet controller 208 may include memory, processors, wired and wireless transceivers for communicating with user device 210. Toilet controller 210 may communicate with remote networks and the Internet.

Figure 3:
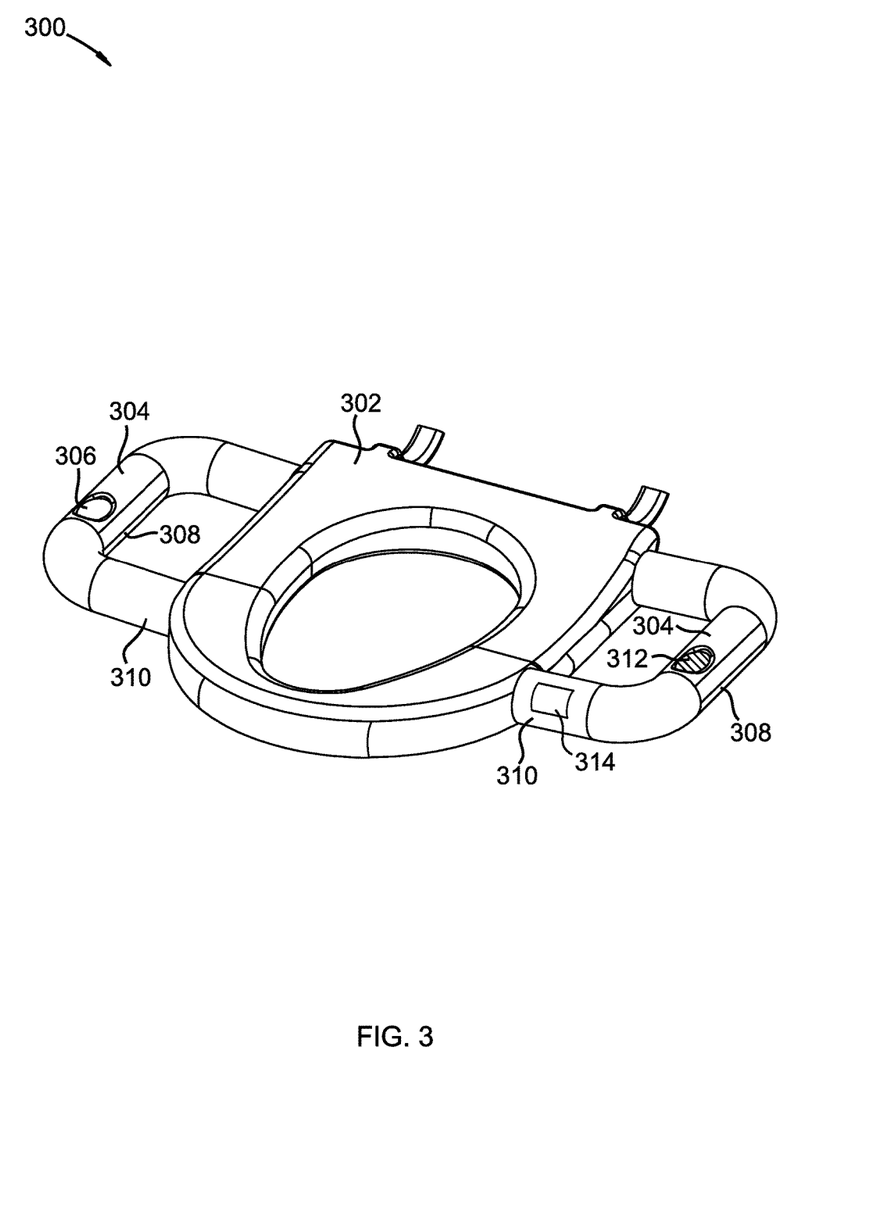
FIG. 3 depicts a perspective view of an instrumented toilet seat.

FIG. 3 depicts a perspective view of an instrumented toilet seat. Toilet seat 300 includes toilet seat 302. Toilet seat 302 includes handles 310. Handles 310 includes fingerprint readers under a transparent surface 306 and 312, top bioimpedance electrodes 304, bottom bioimpedance electrodes 308, transparent surface 306, and lenticular lens surface 312. Though not shown, toilet seat 302 includes a power source and a controller. The power source powers the controller, light transmitters, and light receivers. The controller includes instructions to record photoplethysmographical and bioimpedance data. The controller is coupled to the light receivers and/or light transmitters as well as the bioimpedance electrodes to measure and record data.

Figure 4:
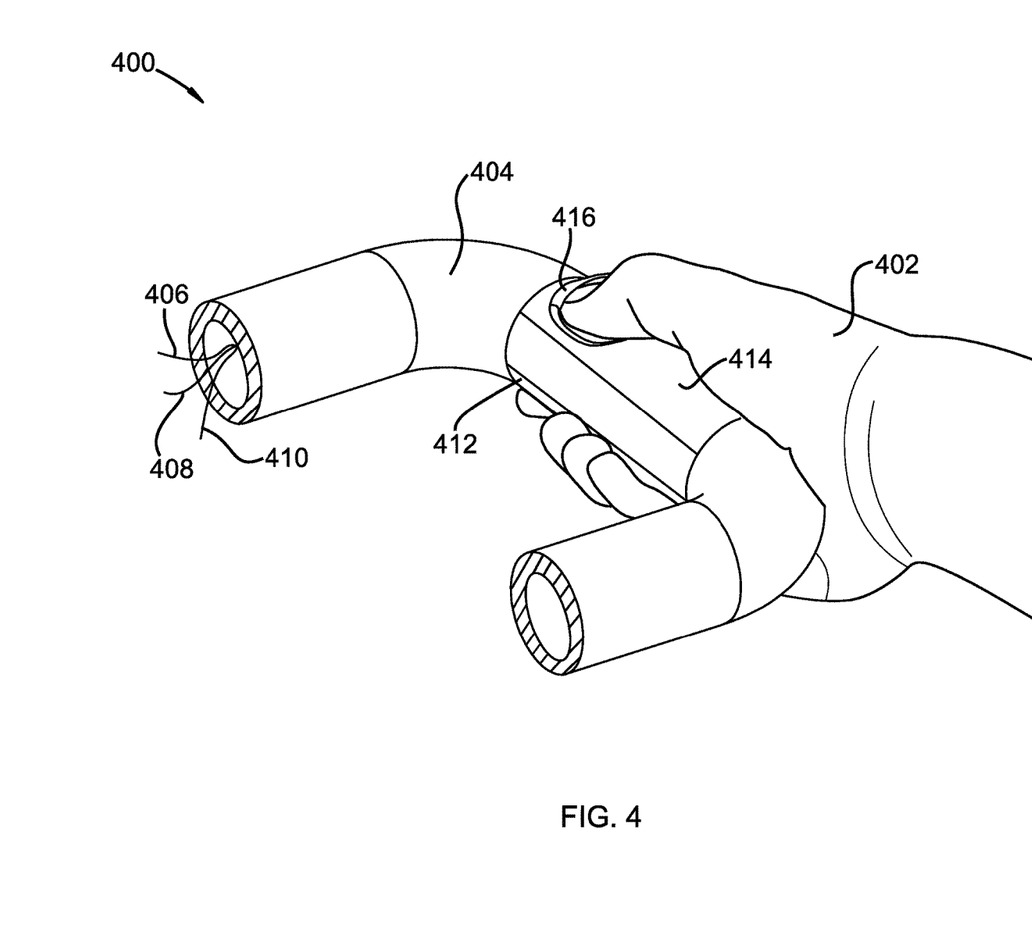
FIG. 4 depicts a perspective view of a handle with a thumb shield.

FIG. 4 depicts a perspective view of a handle with a thumb shield. Toilet seat 400 includes handle 404. Handle 404 includes data wire 406, power wire 408, fiber optic cable 410, top bioimpedance electrode 414, bottom bioimpedance electrode 412, and thumb shield 416. Hand 402 of a user is placed such that a thumb of hand 402 is positioned under thumb shield 416 and pressed against a transparent surface. Underneath the transparent surface is fingerprint reader which emits light signals toward the thumb or a finger of hand 402. The light signals may be partially absorbed by the blood and tissues of the thumb, but parts of the light signals which reflected off of tissues and surfaces of the thumb may be optically detected and surface features of a fingerprint obtained along with blood pulse information.

Data wire 406 transfers data from fingerprint readers, top bioimpedance electrode 414, bottom bioimpedance electrode 412, and/or light receivers to a controller included either in handle 400 or in a toilet seat. Power wire 408 transfers power from a power source to light transmitters, top bioimpedance electrode 414, bottom bioimpedance electrode 412, and/or light receivers. In some embodiments, data wire 406, power wire 408, and fiber optic cable 410 may be contained within a covering which facilitate motion. In these embodiments, handle 404 may move with the motion of hand 402.

Figure 5:
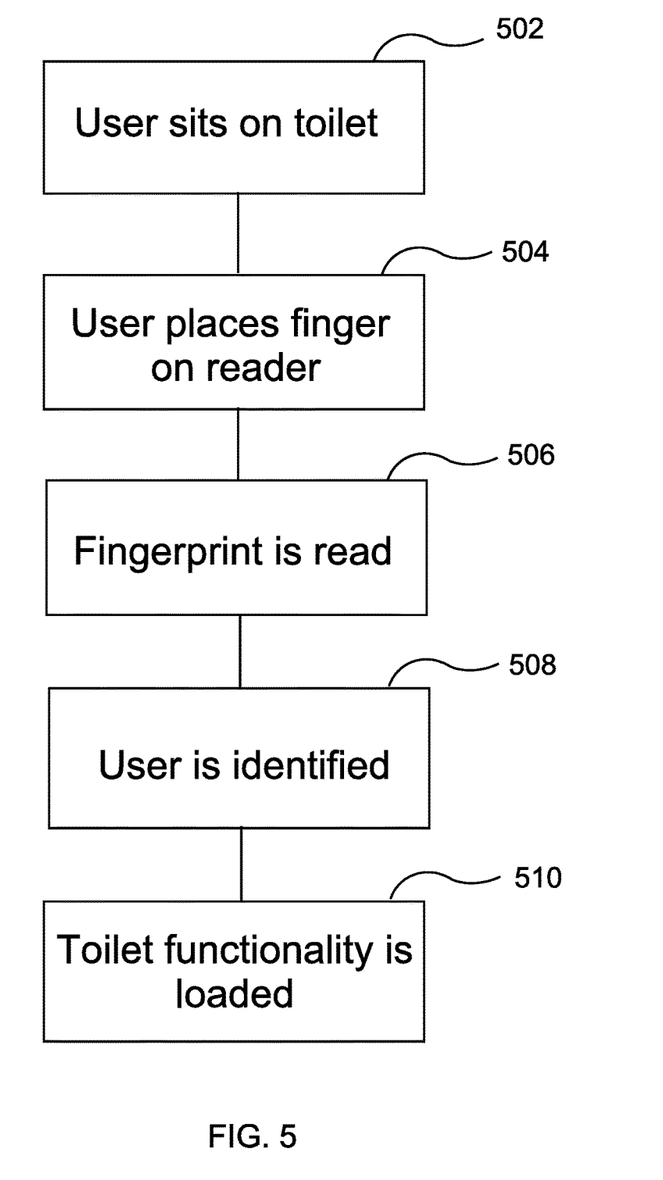
FIG. 5 shows a method of identifying a user and changing one or more functions of a toilet based on the user identification.

FIG. 5 shows a method where a user sits on a medical toilet 502. A fingerprint reader 504 is used to optically detect surface features of a fingerprint and detect color profusion changes within finger tissue. The fingerprint data may be used to authenticate a user of a medical toilet and associate a medical test with the authenticated user. One the user is identified 508, a specific medical test may be loaded from a remote server to the toilet. The functionality of the toilet may be changed based on the loaded toilet settings. For instance, a toilet user may be required to give a urine sample for a pre-employment drug screen. When the user is identified by the toilet, the toilet may be loaded with the data needed to perform the pre-employment drug screen. The toilet may also create an authenticated user data record with a date, time, location, toilet identifier, and medical test identifier associated with the toilet user and store the data in a remote database server such as a medical database server. A toilet may be programmed to perform a specific medical test based on a user identification obtained by fingerprint reader. For example, a doctor may associate a specific test such as a urinalysis, drug test, kidney function test, liver function test, or volatile organic compound test with a specific user identification (fingerprint). When the user's fingerprint is read by a fingerprint reader on a toilet, the toilet may be programmed to perform the medical function (specific test) which a doctor prescribed for the toilet user. The toilet may then authenticate the toilet user and perform the doctor directed testing and report the results to a medical database.

Figure 6:
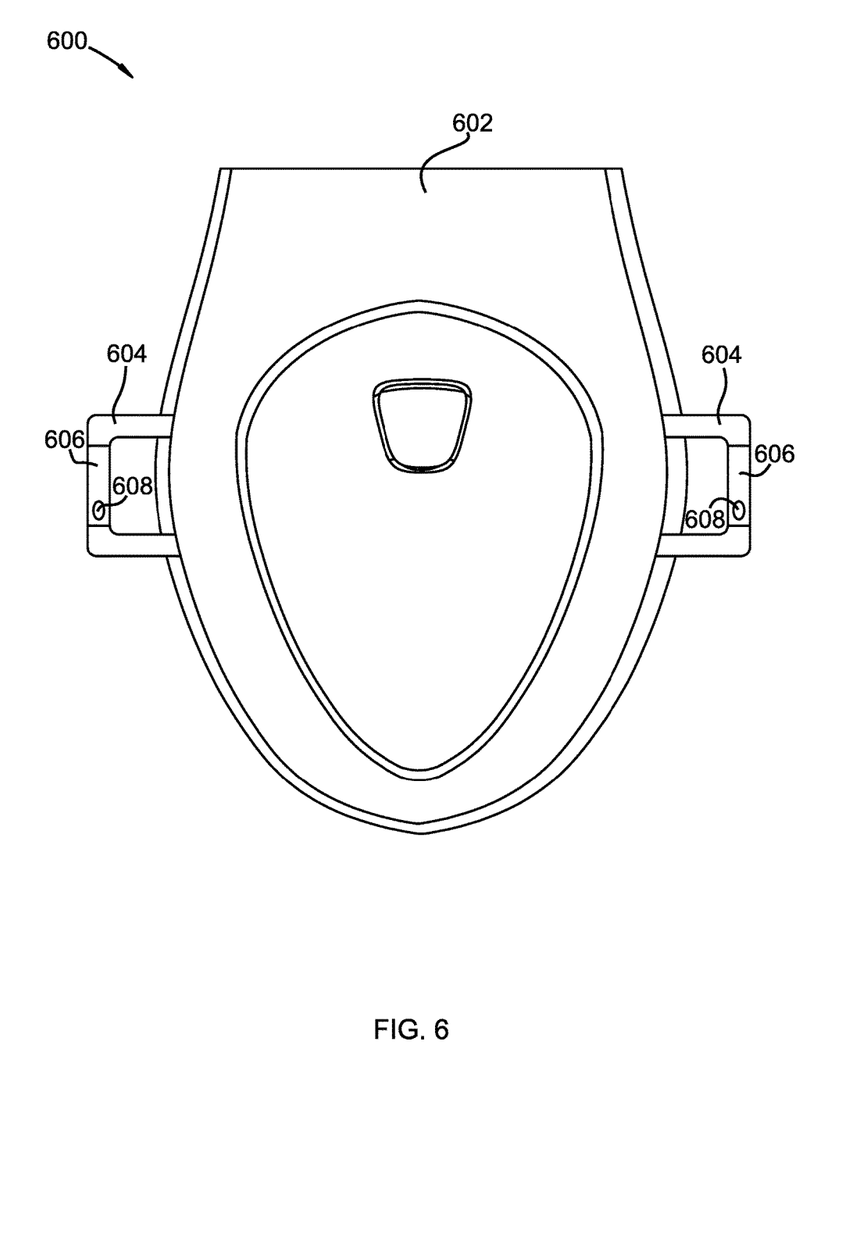
FIG. 6 depicts a top view of a toilet seat.

FIG. 6 depicts a top view of a toilet seat placed on a toilet. Toilet seat 600 includes toilet seat 602. Toilet seat 602 includes multiple handles 604. Handles 604 each include one or more photoplethysmograms 608 and one or more bioimpedance electrodes 606. Though not shown, toilet seat 600 includes a controller and one or more speakers located inside toilet seat 602 and/or handles 604. When a user sits on toilet seat 602, he or she holds handles 604, positioning his or her fingers and palms on fingerprint readers 608. A controller may include instructions to store information received from photoplethysmograms 608 and bioimpedance electrodes 606, to compare the information with previously stored information, to determine which user is sitting on the toilet seat based on the current and previously stored information, and to communicate to the user via the speakers the current information obtained from one or more fingerprint readers and a comparison with the previously stored information.

Figure 7A:
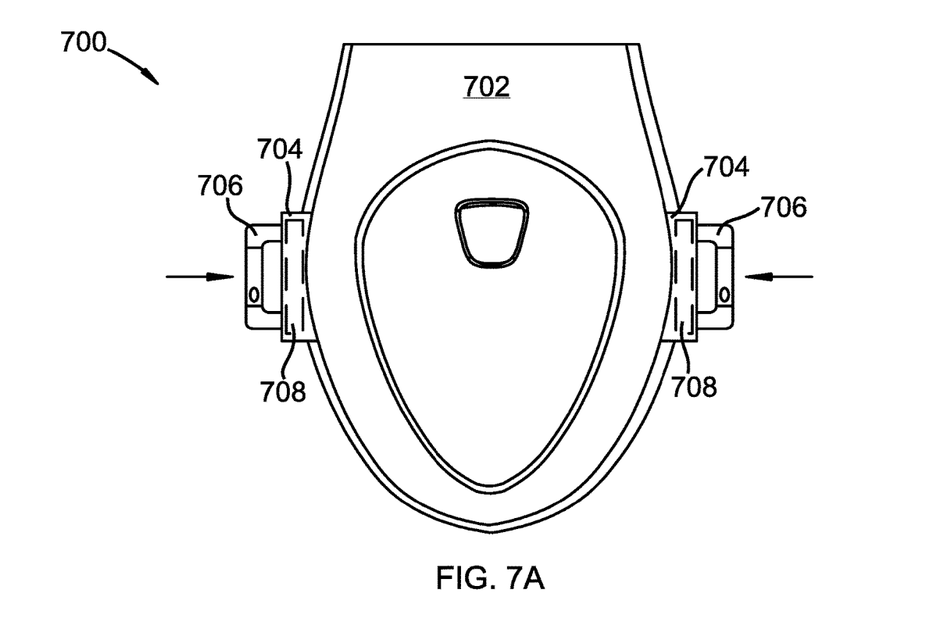
FIG. 7a and FIG. 7b depict a toilet seat with retractable handles.
Figure 7B:
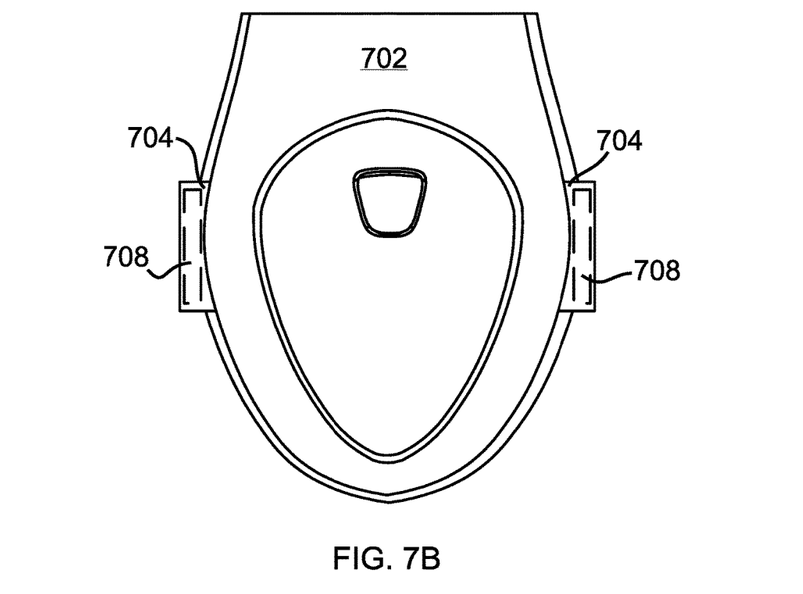

FIG. 7a and FIG. 7b depict a toilet seat with retractable handles. Toilet seat 700 includes toilet seat 702. Toilet seat 702 includes retractable handles 706 and handle-receivers 704. Handle-receivers 704 include cavities 708. When a user is removed from toilet seat 702, handles 706 retract into cavities 708. Handles 706 may be sterilized by ultraviolet (UV) light, emitted either from handles 706 or from UV light emitters positioned within handle-receivers 704. In some embodiments, toilet seat 702 includes force sensors (not shown) and a controller (not shown). When the user is removed from toilet seat 702, the force sensors send data to the controller. The controller includes instructions to retract handles 706 for a specified period and activate the UV light emission. After the specified period, the controller sends electric signals to stop the UV light emission and extend handles 706 to their original position.

Figure 8:
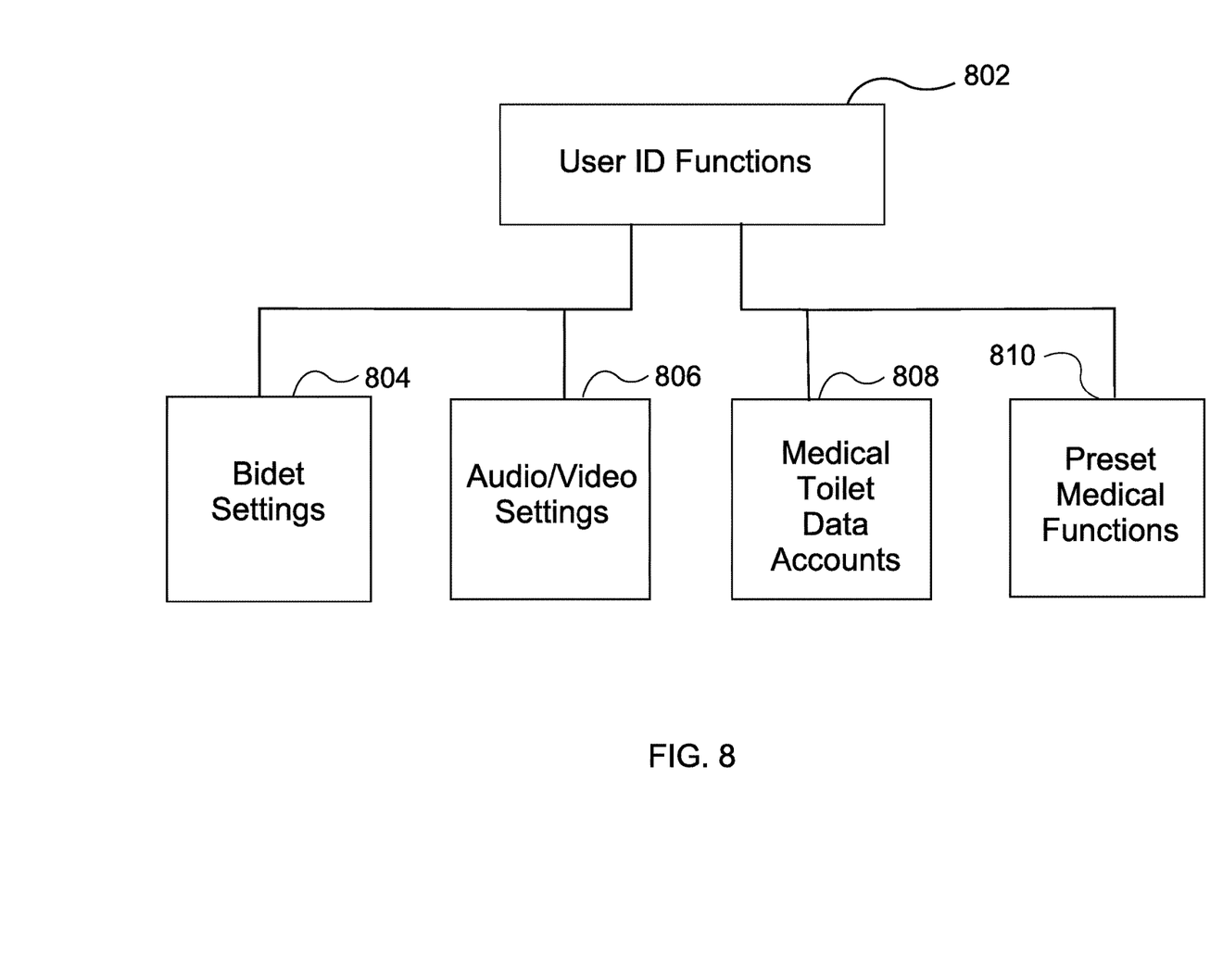
FIG. 8 depicts a block diagram of toilet functions related to a user identification.

FIG. 8 depicts medical toilet functions associated with user identification. When a user is identified, medical toilet settings may be remotely loaded into the toilet. Settings may include: bidet settings 804, audio/video settings 806, medical toilet data account settings 808, and medical toilet function settings 810. Bidet settings 804 may include user settings such as rinse temperature, wash temperature, water pressure settings, bidet wand sprayer position settings, etc. Audio/visual settings 806 may include instructional audio/video related to how to give a sample and step-by-step instructions on how to use the medical toilet. Medical account settings 808 may include settings for reporting medical results of toilet testing to remote medical databases. Medical toilet function settings 810 may include doctor prescribed toilet testing such as: drug testing, urine testing, fecal sample testing, blood sample testing, toxin testing, body composition testing, body weight testing, or cardiac function testing.

Figure 9A:
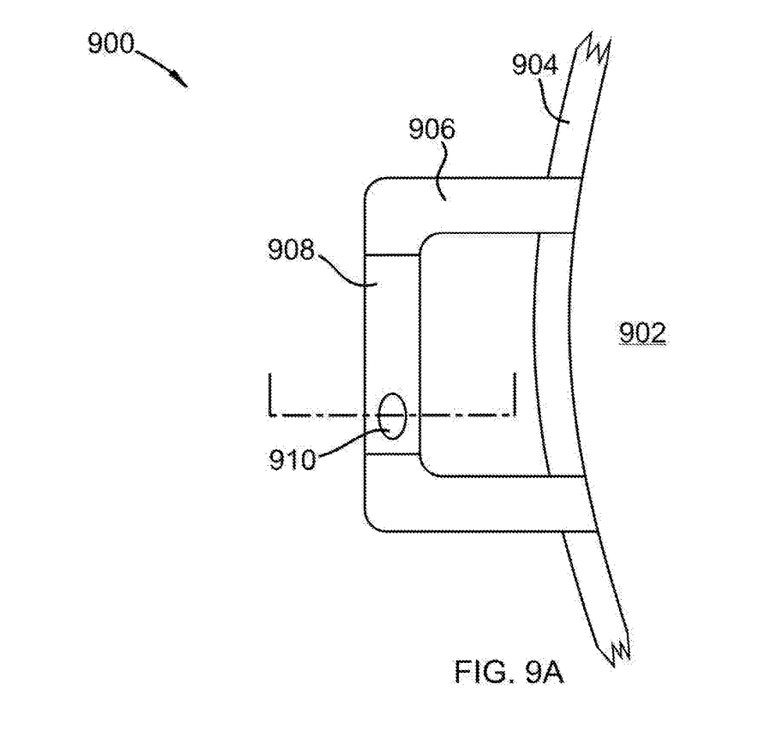
FIG. 9a and FIG. 9b depict a top view and a cross-sectional view of a grooved toilet seat handle with a fingerprint imager.
Figure 9B:
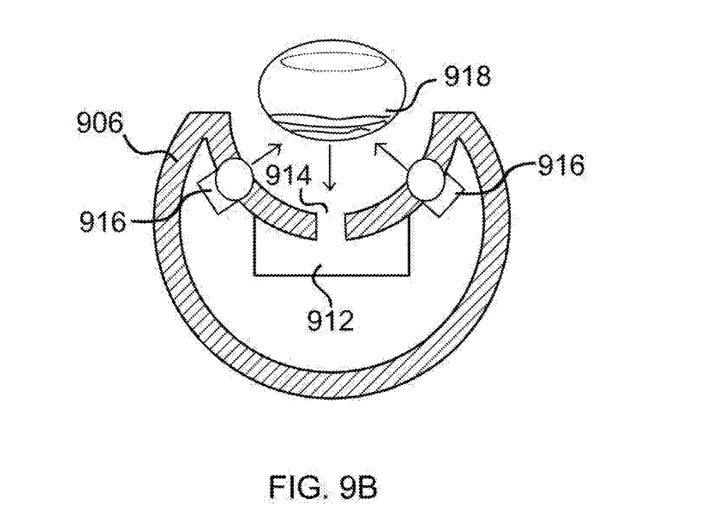

FIG. 9a and FIG. 9b depict a top view and a cross-sectional view of a grooved toilet seat handle with one or more fingerprint readers. Toilet seat 900 includes toilet seat 904. Toilet seat 904 includes one or more handles 906. Handle 906 includes one or more light transmitters 916 and light imagers 912. Each of handles 906 include a recessed section 910, which grooved section 910 may include an aperture 914 and a photodetector, CCD array, or camera 912 positioned at one end of aperture 914. When a user places a finger within the recessed section 910, camera imager 912 uses reflected light image tissue color over time and to image surface features of the fingerprint 918 (described above). A non-contact image may be generated that details surface features of a fingerprint 918. A fingerprint 918 may then be extracted from a digital image. Color change in fingerprint 918 over time can be used to obtain heartbeat other cardiac function information as described earlier. In some embodiments, a reflection PPG sensing operation is utilized. Fingerprint readers employing light transmitters 916 may be positioned on one side of a finger 918 and light receivers 912 may be positioned on the same side of the finger. (Shown in FIG. 9B). In this arrangement, the light transmitters 916 emit light which transmits through one or more top surfaces of tissue and reflects off a lower layer to return to light receivers. Perfusion in capillaries near a surface of skin 918 changes with each heartbeat with phase inverted to transmission PPG sensing. To avoid deep penetration typical of IR wavelengths, which would make a light transmission signal sensitive to arterial behavior and thus reduce the signal resolution due to partial cancellation of an opposing capillary and arterial signals, shorter wavelengths may be desirable. For example, in some further embodiments, light emitted from light transmitters 110 is blue, green, yellow and/or red.

Figure 10:
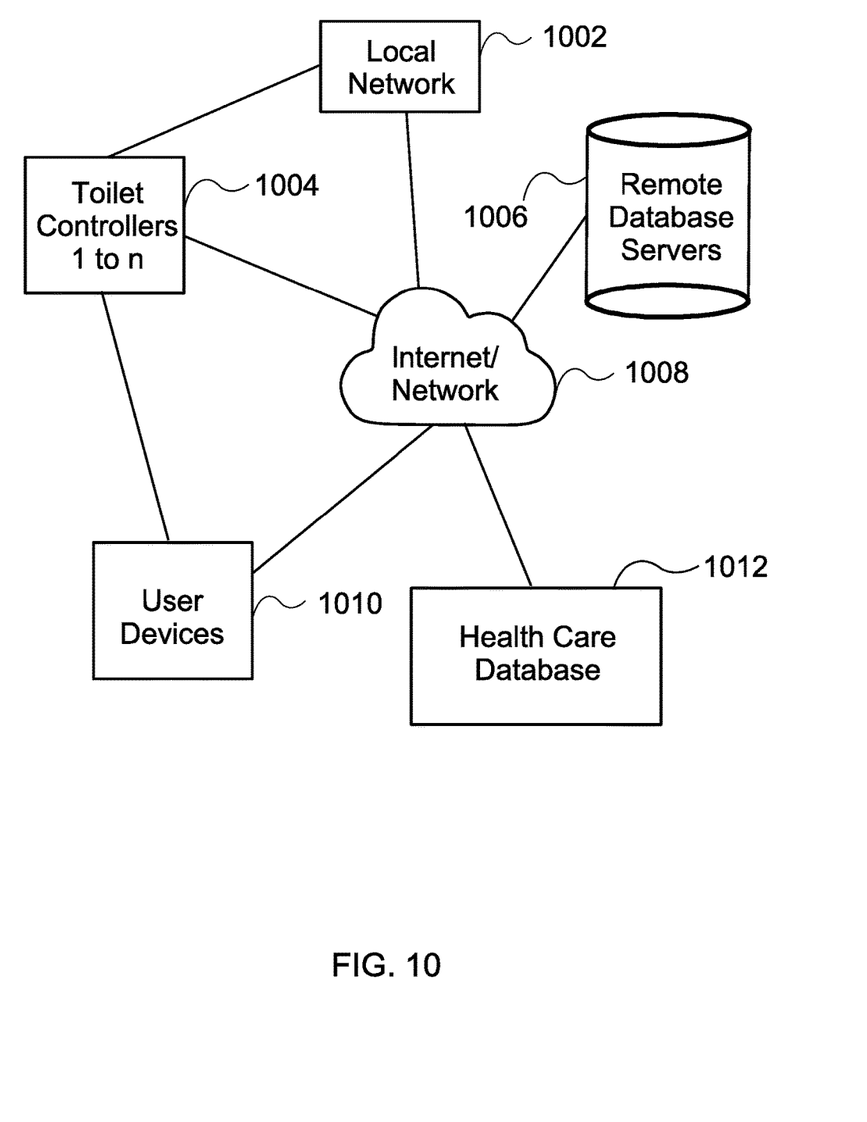
FIG. 10 shows a network data structure related to user identification, authentication, and user account data in accordance with an embodiment of the invention.

FIG. 10 shows a network for obtaining and storing user identification, user authentication, and medical toilet testing functionality and data using a fingerprint reader in toilet seat handles. One or more medical toilets 1004 may be networked together in a local or wide area network. Toilets 1004 may be located at different areas of a hospital, homes, businesses or even in different cities. Each of the toilets 1004 may contain programming and communication hardware allowing communication over the Internet 1008 to remote servers 1006 and databases 1012. User devices 1010 may include phones, computers, iPads, laptops and tables. User devices 1010 may interface directly with medical toilets 1004 or by way of a network connection through a local 1002 or extended network 1008. Fingerprint authentication data may be transferred from medical toilets 1004 to a remote authentication server 1006 or 1012. Once a toilet user is authenticated, medical toilet functional data may be transferred to the toilet 1004 from a remote healthcare database 1012 allowing the toilet to perform a medical function as directed by a healthcare professional. Medical toilet testing may include: drug testing, urine testing, fecal sample testing, blood sample testing, toxin testing, body composition testing, body weight testing, or cardiac function testing.

The invention claimed is:

1. A medical toilet comprising:
a handle which extends from a side of a toilet seat of the toilet allowing a toilet seat user to sit on the toilet seat and access a fingerprint reader located on or within the handle, wherein the fingerprint reader is used to identify the toilet seat user, control medical functionality of the medical toilet, and monitor a cardiac function of the toilet seat user; and
a processor electrically connected to the fingerprint reader programmed to associate the medical toilet, the toilet seat user, the medical functionality of the toilet, and the cardiac function with a user account;
wherein the fingerprint reader is a non-contact fingerprint reader comprising a capacitive coupled display (CCD) imager.

2. A medical toilet comprising:
a handle which extends from a side of a toilet seat of the toilet allowing a toilet seat user to sit on the toilet seat and access a fingerprint reader located on or within the handle, wherein the fingerprint reader is used to identify the toilet seat user, control medical functionality of the medical toilet, and monitor a cardiac function of the toilet seat user; and
a processor electrically connected to the fingerprint reader programmed to associate the medical toilet, the toilet seat user, the medical functionality of the toilet, and the cardiac function with a user account;
wherein the handle comprises an ultrasonic transmitter and an ultrasonic receiver.

3. A medical toilet comprising:
a handle which extends from a side of a toilet seat of the toilet allowing a toilet seat user to sit on the toilet seat and access a fingerprint reader located on or within the handle, wherein the fingerprint reader is used to identify the toilet seat user, control medical functionality of the medical toilet, and monitor a cardiac function of the toilet seat user;
a processor electrically connected to the fingerprint reader programmed to associate the medical toilet, the toilet seat user, the medical functionality of the toilet, and the cardiac function with a user account; and
a speaker system which communicates audio information to a user.

4. The medical toilet of claim 3, wherein the audio information comprises preset audio stored in a database server.

5. The medical toilet of claim 3, wherein the audio information comprises directions by a health care professional on how to give a toilet sample or use the toilet.

6. A medical toilet comprising:
a handle which extends from a side of a toilet seat of the toilet allowing a toilet seat user to sit on the toilet seat and access a fingerprint reader located on or within the handle, wherein the fingerprint reader is used to identify the toilet seat user, control medical functionality of the medical toilet, and monitor a cardiac function of the toilet seat user; and
a processor electrically connected to the fingerprint reader programmed to associate the medical toilet, the toilet seat user, the medical functionality of the toilet, and the cardiac function with a user account;
wherein the handle comprises a visual display; and
wherein the visual display loads a user's preset video settings when the user is identified by fingerprint.

7. A medical toilet comprising:
a handle which extends from a side of a toilet seat of the toilet allowing a toilet seat user to sit on the toilet seat and access a fingerprint reader located on or within the handle, wherein the fingerprint reader is used to identify the toilet seat user, control medical functionality of the medical toilet, and monitor a cardiac function of the toilet seat user; and
a processor electrically connected to the fingerprint reader programmed to associate the medical toilet, the toilet seat user, the medical functionality of the toilet, and the cardiac function with a user account;
wherein the handle comprises a visual display; and
wherein visual display loads video instructions on how to use the toilet or give a toilet sample.

8. The medical toilet of claim 7, wherein the controller comprises one or more light transmitter which interface with fiber optic lines connected to the toilet seat or toilet seat handle.

9. A medical toilet comprising:
a first handle which extends from a side of a toilet seat of the toilet allowing a toilet seat user to sit on the toilet seat and access a fingerprint reader located on or within the handle, wherein the fingerprint reader is used to identify the toilet seat user, control medical functionality of the medical toilet, and monitor a cardiac function of the toilet seat user;
a second handle; and
a processor electrically connected to the fingerprint reader programmed to associate the medical toilet, the toilet seat user, the medical functionality of the toilet, and the cardiac function with a user account;
wherein the user account stores authenticated medical testing data of the toilet seat user; and
wherein the first handle and the second handle retract into the toilet seat and are sanitized by ultra-violet (UV) light.

\* \* \* \* \*